(12) United States Patent
Balme

(10) Patent No.: US 11,471,545 B2
(45) Date of Patent: Oct. 18, 2022

(54) LIGHTING APPARATUS

(71) Applicant: LUXVICI LTD, London (GB)

(72) Inventor: Simon Balme, Brough (GB)

(73) Assignee: LUXVICI LTD, London (GB)

( * ) Notice: Subject to any disclaimer, the term of this patent is extended or adjusted under 35 U.S.C. 154(b) by 0 days.

(21) Appl. No.: 17/184,023

(22) Filed: Feb. 24, 2021

(65) Prior Publication Data

US 2021/0205487 A1 Jul. 8, 2021

Related U.S. Application Data

(63) Continuation of application No. PCT/GB2019/052392, filed on Aug. 27, 2019.

(30) Foreign Application Priority Data

Aug. 24, 2018 (GB) .................................. 1813885

(51) Int. Cl.
| | | |
|---|---|---|
| *A61L 2/00* | (2006.01) | |
| *A61L 2/08* | (2006.01) | |
| *F21V 9/30* | (2018.01) | |
| *F21V 3/08* | (2018.01) | |
| *A61L 2/26* | (2006.01) | |
| *F21V 9/06* | (2018.01) | |
| *F21Y 113/10* | (2016.01) | |
| *F21Y 115/10* | (2016.01) | |

(52) U.S. Cl.
CPC ............... *A61L 2/084* (2013.01); *A61L 2/26* (2013.01); *F21V 3/08* (2018.02); *F21V 9/06* (2013.01); *F21V 9/30* (2018.02); *A61L 2202/11* (2013.01); *F21Y 2113/10* (2016.08); *F21Y 2115/10* (2016.08)

(58) Field of Classification Search
CPC ... A61L 2/084; A61L 2/26; F21V 9/30; F21V 9/06; F21V 3/08
See application file for complete search history.

(56) References Cited

U.S. PATENT DOCUMENTS 7,923,741 B1 4/2011 Zhai et al.
10,286,839 B1 * 5/2019 Mazuir ............... G02F 1/13725
(Continued)

FOREIGN PATENT DOCUMENTS

| WO | 2014042706 A1 | 3/2014 |
| WO | 2015015363 A1 | 2/2015 |
| WO | 2018020527 A1 | 2/2018 |

OTHER PUBLICATIONS

McDonald, RS, et al. "405 Nm Light Exposure of Osteoblasts and Inactivation of Bacterial Isolates from Arthroplasty Patients: Potential for New Disinfection Applications?" European Cells and Materials, vol. 25, 2013, pp. 204-214., doi:10.22203/ecm.v025a15. (Year: 2013).*

(Continued)

*Primary Examiner* — Gerald J Sufleta, II
(74) *Attorney, Agent, or Firm* — Perkins Coie LLP; Viola T. Kung

(57) ABSTRACT

A lighting apparatus for bacterial, fungal and viral disinfection is provided comprising: at least one first element that emits light comprising a peak emission wavelength between at least about 411 nm to up to 419 nm; and at least one second element that outputs and/or converts at least a portion of the light emitted by the first element.

20 Claims, 8 Drawing Sheets

(56) References Cited

U.S. PATENT DOCUMENTS

| | | | |
|---|---|---|---|
| 10,357,582 B1* | 7/2019 | Barron | A61L 2/084 |
| 2015/0162505 A1 | 6/2015 | Jones | |
| 2015/0228868 A1* | 8/2015 | Ouderkirck | F21V 9/38 |
| | | | 362/84 |
| 2016/0093779 A1 | 3/2016 | Maeno et al. | |
| 2016/0372639 A1 | 12/2016 | Mueller et al. | |
| 2017/0030555 A1* | 2/2017 | Lalicki | A61L 2/084 |
| 2017/0045201 A1 | 2/2017 | Jones | |
| 2017/0151359 A1 | 6/2017 | Clynne et al. | |
| 2018/0147417 A1* | 5/2018 | Rantala | H01L 25/0753 |
| 2018/0316160 A1* | 11/2018 | Raring | H01S 5/3203 |
| 2019/0234563 A1* | 8/2019 | Cartiere | F21V 7/22 |
| 2019/0351822 A1* | 11/2019 | Morgan | B60Q 3/64 |
| 2021/0149097 A1* | 5/2021 | Sugio | H01L 33/50 |
| 2021/0184082 A1* | 6/2021 | Stoll | C09K 11/665 |

OTHER PUBLICATIONS

International Search Report and Written Opinion for PCT/GB2019/052392, dated Dec. 4, 2019, 13 pages.
GB Search Report for Application No. GB1813885.9, dated Feb. 14, 2019, 5 pages.

* cited by examiner

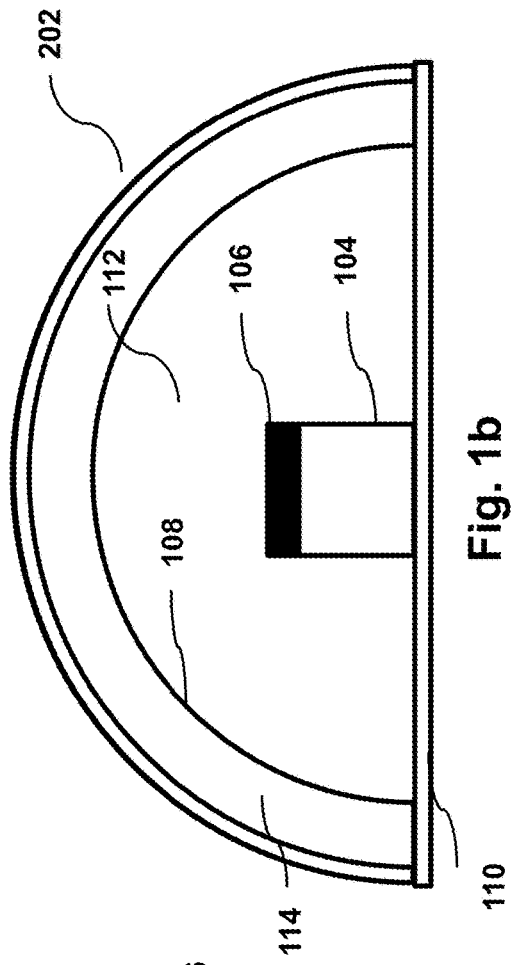
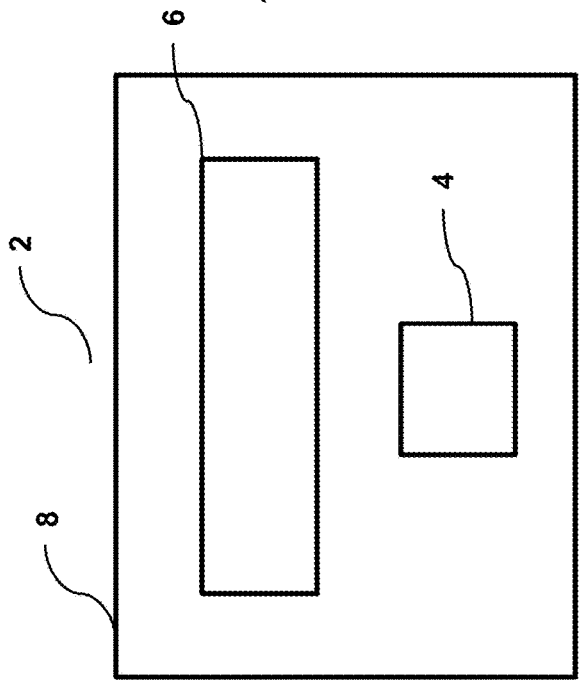
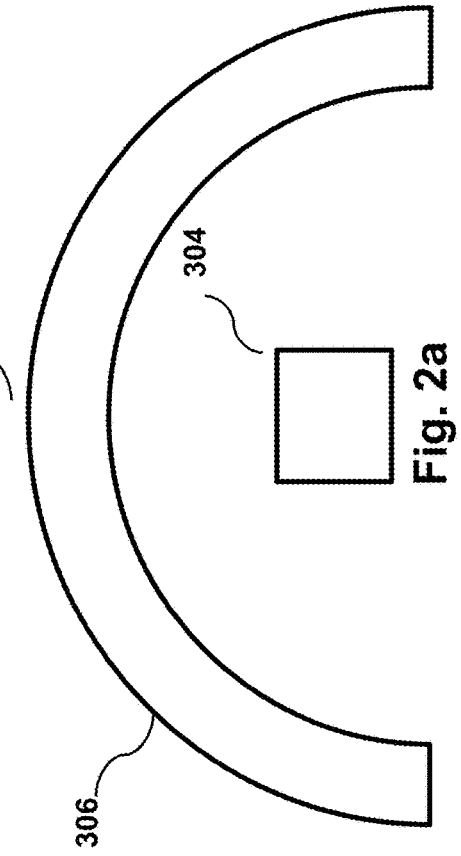
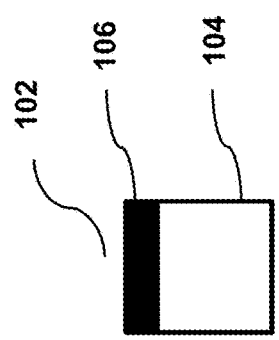

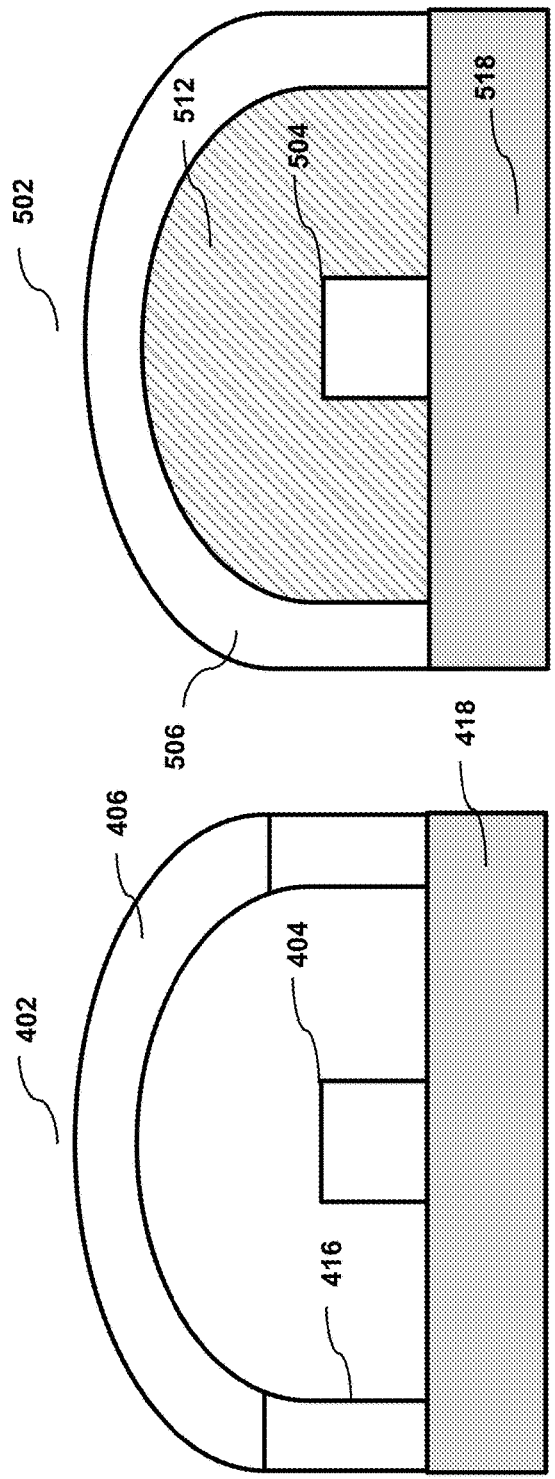
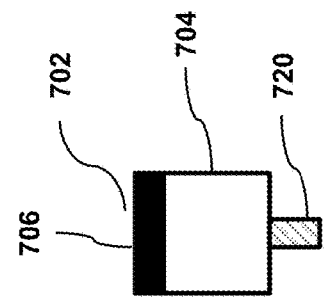
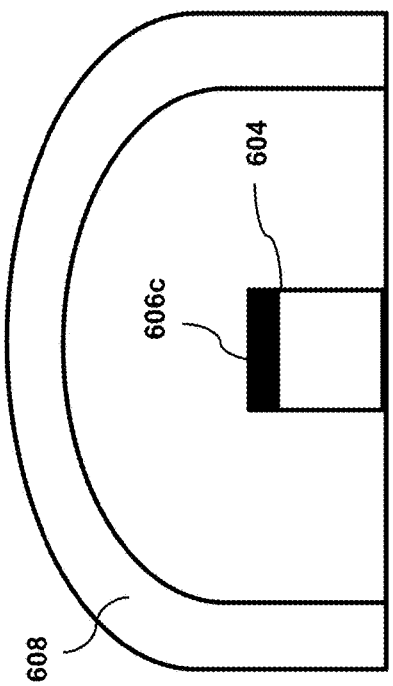

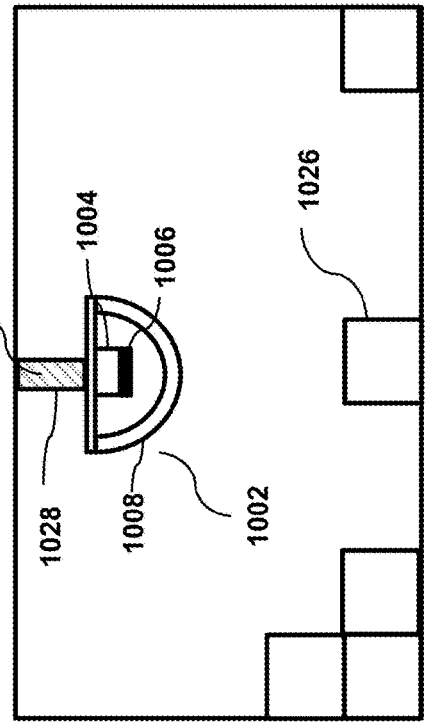
Fig. 3
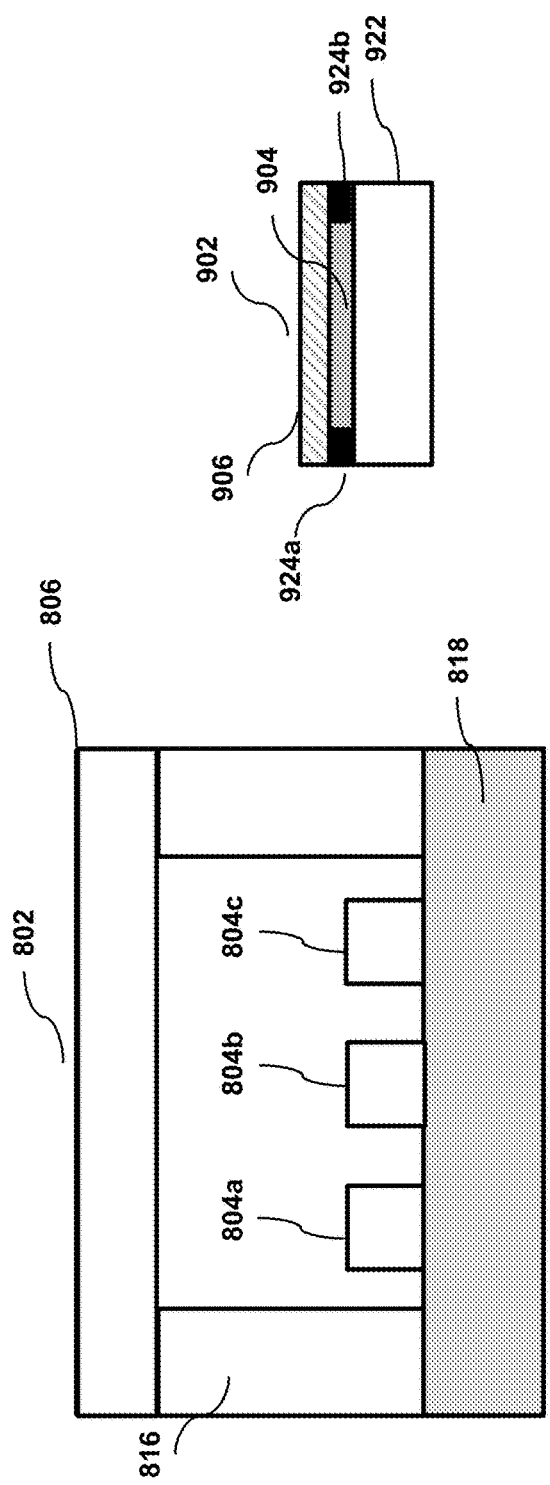
Fig. 4
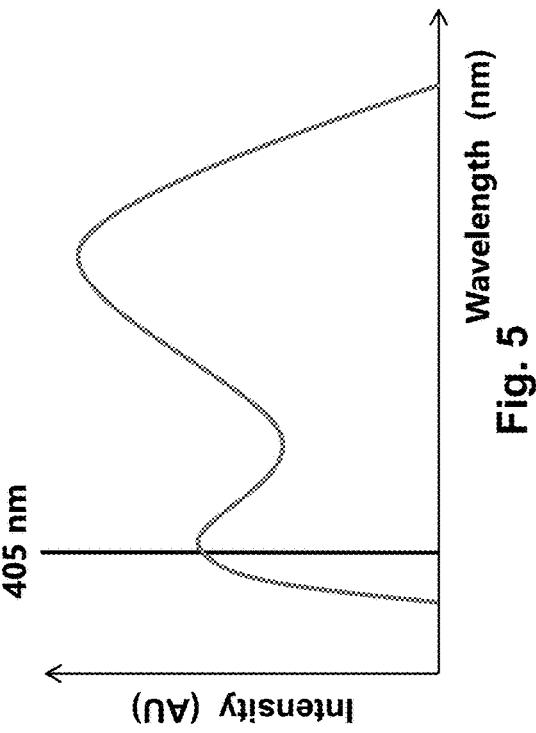
Fig. 5
Fig. 6

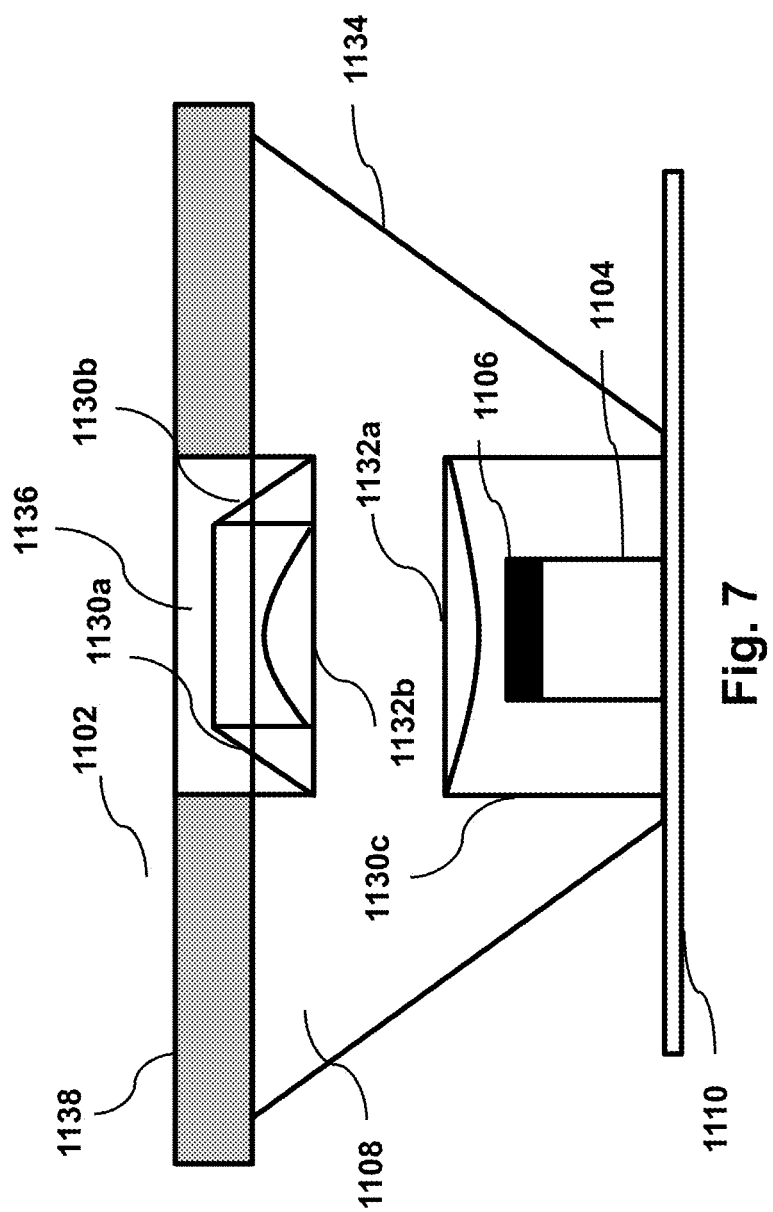

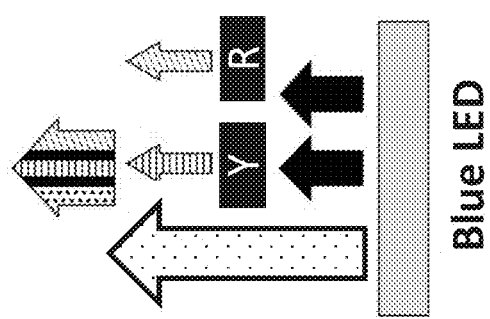 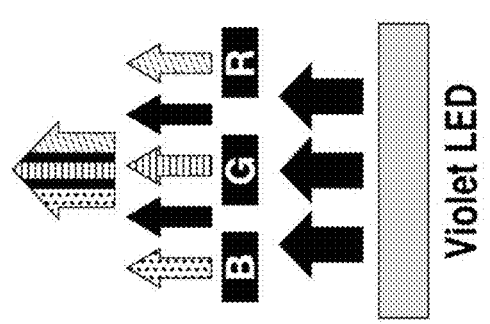
Fig. 9a
Fig. 9b

LIGHTING APPARATUS

This application is a continuation of PCT/GB2019/052392, filed Aug. 27, 2019; which claims the priority of GB 1813885.9, filed Aug. 24, 2018. The contents of the above-identified applications are incorporated herein by reference in their entirety.

FIELD OF THE INVENTION

The field of the invention is in lighting apparatus, particularly, but not exclusively lighting apparatus emitting one or more wavelengths used to control bacterial growth.

BACKGROUND

Various lighting systems exist and may have different optical emission properties and uses dependent upon where they are installed and what functions are required of them. Typically, a room may be required to have white light illumination however other lighting sources may be needed in the room for other purposes. One such purpose may be for bacterial control. This may be particularly relevant for areas where a higher degree of bacterial growth control is necessary, for example hospitals and other areas where people's medical considerations are of high priority. Having to illuminate an area with multiple separate light sources for different purposes leads to issues of: extra cost for purchasing and installing the different lighting devices; the need for the facilities for locating and driving the different lighting devices.

Certain light apparatus use a plurality of LEDS or sources of light so the lighting apparatus covers the desired light output spectrum. The light output can be generally white from a mix of red, green, blue (RGB) sources or from various colourisation or filtering technologies to modify the light source spectra to create the desired light output spectrum from the lighting apparatus. Lighting apparatus using a variety of different wavelength LEDs or other light sources to output the desired broad spectra present a number of issues. The issues include optical colour control issues and colour maintenance problems. The lighting solution therefore needs to take this into account and typically requires continued monitoring to maintain the desired light output spectra. The extra systems or user time required for this may be impractical.

Antibacterial lighting sources, and other light sources, often emit actinic radiation or sometimes referred to as light in the UV (Ultra Violet) wavelength range. Actinic radiation is known to have an adverse effect on humans giving rise to medical conditions such as skin cancers (melanoma) and cataracts. Actinic radiation can also have detrimental effects generally on non-organic objects and materials. One such effect is UV bleaching where UV rays break down the chemical bonds and cause an object's colour to fade. Using UV in lighting systems to control bacterial growth therefore has disadvantages that a lighting designer needs to overcome. Typical ways to overcome this include reducing exposure time of the actinic radiation, for example pulsing or otherwise turning the UV portion of the light on/off. Doing this increases the complexity of the lighting solution.

SUMMARY

In a first aspect of the invention there is provided phosphor lighting apparatus comprising:

at least one first element that emits light comprising a peak emission wavelength between at least about 411 nm to up to 419 nm; and, at least one second element comprising phosphors that output and/or convert at least a portion of the light emitted by the first element;

wherein the light output from the phosphor lighting device comprises light emitted from the first element and light emitted from the phosphors.

The first aspect may be modified in any suitable way described herein, including but not limited to any one or more of the following options.

The first element may emit light comprising a peak emission wavelength of any of 412 nm-415 nm.

The first element may emit light with a full width at half maximum (FWHM) of up to 10 nm.

The first element may emit at a peak emission wavelength of 412 nm.

The first element peak emission wavelength may be between 410 nm and 414 nm.

The lighting apparatus may comprise: at least one first element that emits light comprising a peak emission wavelength between at least about 400 nm to up to but not including 420 nm; and, at least one second element that outputs and/or converts at least a portion of the light emitted by the first element.

The lighting apparatus may comprise a light emitting diode (LED) first element.

The lighting apparatus may comprise a second element emitting light comprising longer wavelengths than the peak emission wavelength of the first element.

The lighting apparatus may comprise at least one second element comprising any one or more of colour conversion elements selected from the group comprising: coloured filters, phosphors and quantum dots.

The lighting apparatus may comprise at least one second element comprising a material applied upon the first element.

The lighting apparatus may comprise a second element comprising phosphors for absorbing light from the first element and emitting light at longer wavelengths than the absorbed light.

The lighting apparatus may comprise phosphors comprising a yellow phosphor.

The lighting apparatus may comprise a second element comprising one or more colour converting materials selected from the group consisting of: nitride and/or oxynitride; YAG phosphor, zinc sulfide, zinc selenide, cadmium sulfide, cadmium selenide, cadmium telluride and combinations thereof.

The light emitted by the first element may comprise a lower FWHM wavelength that is above 405 nm.

The lighting apparatus may comprise a first element emitting light comprising a peak emission wavelength between at least about 400 nm and at most about 410 nm.

The lighting apparatus may comprise a plurality of first elements.

The lighting apparatus may comprise at least one of the second elements comprising an optical filter for filtering actinic radiation emitted from the first element.

The lighting apparatus may comprise an actinic radiation filter which is configured to receive light emitted from the first and second elements; and transmit actinic radiation filtered light for outputting by the lighting apparatus.

The optical output power of the lighting apparatus may correspond to wavelengths above 400 nm.

The combined output of the first element and the second element may be white or a shade of white light.

The lighting apparatus may be for general illumination, for example, for lighting a room. The lighting apparatus may comprise electronics configured to at least provide electrical power to the first element.

The electronics may be configured to drive the first element to output continuous wave light.

According to a second aspect of the present invention, there is provided a phosphor lighting device comprising:
- at least one LED that emits light comprising a peak emission wavelength between 411 nm up to 419 nm; and,
- at least a second element located on at least a portion of the LED and comprising phosphors that:
  - absorb at least a portion of light emitted from the LED; and,
  - emit light at a peak emission wavelength that is longer than the peak emission wavelength of the LED;
- wherein the light output from the phosphor lighting device comprises light emitted from the LED and light emitted from the phosphors.

The second aspect may be modified in any suitable way described herein including, but not limited to, any one or more of the optional features for the first aspect described above and/or any one or more of the following options.

The LED may emit light comprising a peak emission wavelength of 412 nm.

The LED may emit light comprising a peak emission wavelength of any of 412 nm-415 nm.

The LED may emit light comprising a full width at half maximum (FWHM) of 10 nm.

The LED may comprise a lower FWHM wavelength that is above 405 nm.

LED peak emission wavelength may be between 410 nm and 414 nm.

The phosphor lighting device may comprise: at least one LED that emits light comprising a peak emission wavelength between 400 nm up to but not including 420 nm; and, at least a second element located on at least a portion of the LED and comprising phosphors that: absorb at least a portion of light emitted from the LED; and, emit light at a peak emission wavelength that is longer than the peak emission wavelength of the LED; wherein the light output from the phosphor lighting device comprises light emitted from the LED and light emitted from the phosphors.

The phosphor lighting device may comprise an LED peak emission wavelength between 400 nm and 410 nm.

The phosphor lighting device may comprise phosphor comprising a YAG phosphor.

The phosphor lighting device may comprise at least one of the second elements comprising an optical filter for filtering actinic radiation emitted from the first element.

Substantially all of the optical output power of the said phosphor lighting device may correspond to wavelengths above 400 nm.

According to a third aspect of the present invention there is provided a method of assembling a lighting apparatus as described in the first aspect and optionally any one or more of its optional features, the method comprising locating the first and second element in a housing.

The third aspect may be modified in any suitable way described herein including, but not limited to, any one or more of the following options.

The method may comprise, prior to locating the first and second element in the housing, depositing the second element on the first element.

The method may further comprise sealing the housing after locating the first and second elements in the housing.

According to a fourth aspect of the present invention there is provided a method of assembling a lighting apparatus as described in the first aspect and optionally any one or more of its optional features, the method comprising depositing the second element on the first element The third aspect may be modified in any suitable way described herein including, but not limited to, any one or more of the following options.

The method may comprise locating the first and second element in the housing.

The method may further comprise sealing the housing after locating the first and second elements in the housing.

BRIEF DESCRIPTION OF THE FIGURES

FIG. 1 shows a schematic example of a lighting apparatus;

FIG. 1a shows an example of a lighting apparatus comprising a phosphor layer coated upon an LED chip;

FIG. 1b shows an example of the lighting apparatus of FIG. 1a located on a board and having a housing;

FIG. 2a shows an example of the lighting apparatus comprising a remote phosphor layer;

FIG. 2b shows an example of the lighting apparatus of FIG. 2a located on a substrate for attaching to a light fitting;

FIG. 2c shows another example of the lighting apparatus having an encapsulant between the first and second elements;

FIG. 2d shows another example of the lighting apparatus similar to FIG. 2c wherein the second element is coated on the first element;

FIG. 2e shows the example of the first element and second element of FIG. 2d without an outer housing and having an attachment means;

FIG. 3 shows an example of the lighting apparatus comprising a remote phosphor layer and three LEDs;

FIG. 4 shows an example of an LED for use with the lighting apparatus;

FIG. 5 shows an example of an output spectrum of the lighting apparatus;

FIG. 6 shows the use of the lighting apparatus in residential and commercial spaces;

FIG. 7 shows another example of the lighting apparatus similar to FIG. 1a and having primary and secondary optical elements.

FIG. 9a shows a schematic drawing of a lighting apparatus having an emission spectrum dissimilar to sunlight; FIG. 9b shows a schematic drawing of a lighting apparatus having an emission spectrum similar to sunlight.

FIG. 10b shows a top view of the lighting apparatus of FIG. 10a.

DETAILED DESCRIPTION

Figure 8A:
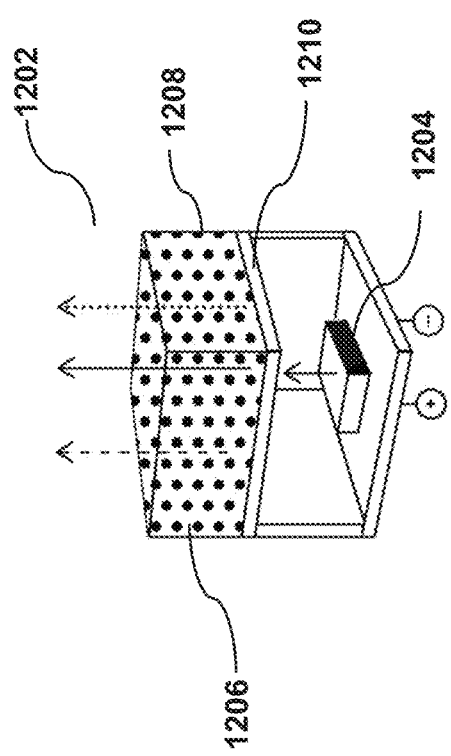
FIG. 8a illustrates an example lighting apparatus having a transparent substrate.

There is presented a lighting apparatus comprising: at least one first element that emits light comprising a peak emission wavelength between at least about 400 nm to up to but not including 420 nm; and, at least one second element that outputs and/or converts at least a portion of the light emitted by the first element.

There is also presented a lighting apparatus comprising at least one first element that emits visible light at a peak emission wavelength from at least about 400 nm to up to but not including 420 nm. FIG. 1 shows a schematic example of this lighting apparatus. The lighting apparatus further comprises at least a second element that emits light a) at a peak emission wavelength that is longer than the peak emission wavelength of the first element; b) using at least a portion of the light emitted by the first element in a photoluminescence process.

Alternatively, there is presented a lighting apparatus comprising at least one first element that emits visible light at a peak emission wavelength between at least about 400 nm to up to but not including 420 nm. The lighting apparatus further comprises at least a second element that outputs light a) at a peak emission wavelength that is different than the peak emission wavelength of the first element; b) using at least a portion of the light emitted by the first element through reflection and/or filtering.

The lighting apparatus may be adapted according to any feature or configuration described herein.

The lighting apparatus may be equipped with an optical filter for filtering at least a portion of the light emitted by the first element. This may be beneficial to filter any residual UV-light emitted by the first element. Deployment of a filter may also be beneficial to control the bandwidth of the LED emission. The second element described above may comprise the optical filter. Such a filter may be an absorptive filter usually made from glass, polycarbonate or acrylic. Alternatively, dichroic filters (reflective filters) may be used. Dichroic filters can be manufactured by depositing (e.g. by vacuum deposition) optical coatings with different refractive indices onto a glass substrate. The use of dichroic filters allows for control of the exact color range since the thickness as well as the nature and sequence of the coating layers can be varied. The optical filter may be used solely in combination with the first element as a second element or additionally to a first and a second element.

The lighting apparatus may further be equipped with one or more reflector(s) to propagate light into parallel rays or collimate light. The second element described above may comprise the one or more reflector(s). The light is propagated by positioning and angling the reflective surface of the reflector with respect to the light source so the output path of the light reflected from the reflecting surface is parallel. The reflecting surface may be manufactured by faceting, segmenting or coating of the inner surface of the first element with for example aluminium or reflective polymers. Total internal reflection (TIR) optics may also be used. In lighting devices where total internal reflection is used a lens guides the light from the first element to a reflector which outputs a controlled light beam. TIR optics can be injection moulded from polymers and tailored to the desired beam pattern by for example rippling, pillowing or polishing. In order to direct light onto a target, secondary optics such as a secondary lens may be used. The reflector including TIR optics may be used solely in combination with the first element or additionally to a first and a second element.

There is further presented, in one example of the lighting apparatus, a remote phosphor lighting device for viral, bacterial and fungal disinfection. The device comprises at least one LED that emits visible light at a peak emission wavelength between 400 nm up to but not including 420 nm. The device further comprises at least a second element comprising phosphors that: i) absorb at least a portion of light emitted from the LED; and, ii) emit light at a peak emission wavelength that is longer than the peak emission wavelength of the LED. The light output from the remote phosphor lighting device comprises light emitted from the LED and light emitted from the phosphors.

There is also presented, in one example of the lighting apparatus, a lighting device for viral, bacterial and fungal disinfection. The device comprises at least one LED that emits visible light at a peak emission wavelength between 400 nm up to but not including 420 nm. The device further comprises at least a second element comprising a filter and/or a reflector outputting light at a peak emission wavelength that is different than the peak emission wavelength of the LED. The light output from the lighting device comprises light emitted from the LED and light output by filtering and/or reflection.

This example may be adapted according to any feature or configuration described herein.

The light emitted by the first element has an inhibiting effect on at least certain types of bacteria. Further details on this are discussed underneath. By having a lighting apparatus that emits light to control bacterial growth and uses a portion of the emitted light to facilitate the emission of other light wavelengths, for example in the visible spectrum, the lighting apparatus can therefore be used in general illumination applications but have inherent bacterial control. This bacterial control is present when the light is operating normally. For purposes of discussing the lighting apparatus in the present disclosure the light emitted by the first element may be referred to as the 'active wavelength'.

For example, a lighting apparatus is used to illuminate a room and has phosphors that absorb a portion of the light emitted by the first element and in turn emit light of other wavelengths so that the overall light output from the lighting apparatus is deemed a 'white' light. This white light not only illuminates the room but also as part of its normal emission spectra emits wavelengths that help control bacterial growth.

A user or a system controlling the light therefore does not have to purchase or install a separate light to control the antibacterial growth, although in principle the lighting apparatus of the present application may utilise control systems and sensors to affect the operation of the lighting apparatus if needs require. Furthermore, the lighting apparatus may be run and output the active wavelength without a sensor or human input being required to turn on or off the lighting part emitting the active wavelength.

The lighting device may further comprise an optical fibre wherein the combined light output from the phosphors and the first element is focused by focusing optics into an optical fibre. The focusing optics comprising any of: one or more mirrors, one or more lenses or other optical components. The other end of the optical fibre outputs the light may be used to illuminate an object, for example, being inserted into a portion of a human or animal body. Having bacteria killing light illuminate. The light from the source may also be focused into a bundle of optical fibres. A medical professional performing an operation or investigating the inside of a human or animal body may therefore illuminate an area for inspection wherein the light used for illumination may be also acting to kill bacteria, hence helping prevent infection.

For existing systems that use other wavelengths, for example UV (discussed below) to control bacterial growth, these systems typically need to cycle or otherwise control the amount of the light output at the active wavelength of these existing system. This may require control electronics and/or sensors to determine the optimum times to turn the antibacterial control wavelengths on or off. These existing systems may drive the antibacterial light in a pulsed manner, which again requires extra electronics to facilitate the appropriate drive signal and may degrade the lighting apparatus from the continued turning on or off.

In some examples the lighting apparatus emits substantially no actinic radiation. These examples may be where the light source used for the first element emits substantially no optical power in the UV. Additionally or alternatively, this may be where the second element has a UV filter for receiving the light emitted by the first element and filters the light to remove the UV wavelengths. The electromagnetic spectrum of actinic radiation (UV) is defined by a wavelength range of 100 nm to 400 nm according to ISO 21348. Subtypes of actinic radiation include UVA (315 nm to 400 nm), UVB (280 to 315 nm) and UVC (100 to 280 nm). These ranges have been established based upon the atmosphere's capability to absorb UVA, UVB and UVC radiation.

The UVA content of the sunlight is not absorbed by the ozone layer and therefore most people are exposed to large amounts of UVA radiation throughout their lifetime. UVA radiation is known to cause skin-aging and is also believed to be involved in the development of certain types of melanoma (skin cancer). More specifically, exposure to UVA radiation can damage skin cells called keratinocytes in the upper layer of the epidermis, which is where most skin cancers occur.

The higher energetic UVB content of the sunlight is partly absorbed by the ozone layer and is known to cause sunburn and damage superficial epidermal skin layers. It is also well known that exposure to UVB radiation is linked to the development of skin cancer.

UVC is highly energetic radiation and all solar UVC is absorbed by the atmosphere. UVC is known to be a highly effective germicide due to its ability to damage DNA.

Existing anti-bacterial light engines contain actinic radiation with various levels of UVA-UVB-UVC. These wavelengths are damaging to both bacterial and mammalian cells. They also have a degrading effect on materials and are a risk to humans under the CIE guidelines on blue light exposure. They have a greatly reduced effect on bacteria (especially gram negative), and are thereby not very energy efficient. As discussed in *Scientific Reports* volume 8, Article number: 12722 (2018), the UV/Visible radiation boundary region (385-405 nm) damages skin cells and induces "dark" cyclobutane pyrimidine dimers in human skin in vivo.

Other advantages of using light within the range of around 400-420 nm is that blue light with wavelengths greater than 420 nm have been proven to cause changes that resemble those of macular degeneration which lead to permanent vision loss. These wavelengths also affect the regulation of the circadian rhythm, the body's natural sleep-wake cycle. The same advantages may be achieved with other wavelength ranges between 400-420 nm described elsewhere herein.

Having a lighting apparatus that uses a blue/violet component that does not lead to or has a lesser propensity to give rise to these undesirable effects, is therefore beneficial.

As mentioned elsewhere in the application, a first element having peak emission wavelength between 400 nm up to but not including 420 nm may be used in combination with a for example UV-filtering element, wherein the second element has this filtering element. This is particularly advantageous for applications which do not necessarily require white light illumination but where the lighting apparatus is used in environments where humans are present. This may be useful for example in food systems, water systems or display applications. Additionally, if a white light system is used, for example by the second element having phosphors, a further second element having a UV filter may also form part of the lighting apparatus. This provides a white light source for illuminating an area that has an adverse effect on bacteria, whilst not outputting damaging UV light. This white lighting apparatus is particularly beneficial in certain scenarios, for instance when the light is installed into a room such as a hospital room. This white lighting apparatus could be a light bulb that can be fitted into a standard light fitting such as a ceiling light and may replace an existing bulb.

Systems, wherein a first element having peak emission wavelength between 400 nm up to but not including 420 nm is used in combination with a filtering and/or reflecting element may be particularly advantageous for certain applications. Those applications may be providing general lighting, for example ambient lighting, in a local area such as a room. Light emitted from the first element can be focused and directed to illumination of a whole room or specific areas. Focusing of the light could be achieved be a reflecting surface or a transmission lens. The reflecting surface may be curved to reflect and focus the light. Alternatively the second element may have a reflecting surface or a lens that causes the light to diverge.

The second element generally may comprise a lens or other refracting element and/or a diffracting element for focusing or otherwise directing the light output from the apparatus. The lens may be a convex or concave lens that directs light into a local environment. Unlike existing systems that use actinic radiation in a simple manner, the lighting apparatus may provide a first element that outputs light radiation for inhibiting bacterial growth and a second element to direct the said light in a manner suitable for illuminating the local environment.

The lighting apparatus may be used in a number of scenarios and lighting environments. These include any one or more of, but not limited to: an environment where a system is required to affect antibacterial resistant strains of bacteria; an environment where it is desirable to control cross contamination via air conditioning systems, such as an HVAC system; an environment where it is desired to control bacterial growth within fluids, water, blood, food items; an environment where it is desired to control bacterial contamination of devices such as Head Up Displays (HUD) and touch screens; an environment where it is desired to aid reduction of chemical dependency to control bacteria; an environment where it is desired to reduce impact on the eco-system by not using non-degradable chemical alternatives i.e. bleach, triclosan.

The lighting apparatus may be used in residential and commercial spaces such as kitchens, lavatories, bars, office spaces, HVAC systems, prisons, hospital, residential homes, military bases; during food preparation such as food manufacturing, food transportation; in vehicles and more specifically emergency vehicles, ambulances and public transport; and in displays such as in head-up displays (HUD), mobile phone displays and white goods.

The lighting apparatus may be a lighting device such as but not limited to: a light bulb, a lamp, a lighting component including an LED, a light engine (components to go into a light fixture), a panel light, any sort of fixture including those used for surgery.

Typical light fittings for the lighting apparatus may include bayonet caps (for example SBC B15d, BC B22d), Edison screw Caps (for example MES E10, SES E14, ES E27, GES E40), halogen capsule pins (for example G4, GY6.35), liner halogen capsule caps (for example R7S), halogen and LED spotlight fittings with and without bevel (for example GU4, GU5.3, GU10, GZ10), fluorescent tube and LED tube fittings (for example G5, G13), architectural strip light fittings (for example S15s, S14s, S14d), push fit light bulb fittings (for example G23 2 pin, 2G7 4-pin, 2G11 4-pin, G24d-1 2-pin, G24d-2 2-pin, G24d-3 2-pin)

The First Element

The first element may emit visible light. The peak emission wavelength may be at least about 400 nm, typically about 410 nm, suitably about 405 nm. The peak wavelength of the emission from the first element may be a peak wavelength in the range of 400-420 nm, or 400-419 nm, 407-417 nm or 401-420 nm, or 401-419 nm. Other peak wavelengths and peak wavelength ranges discussed herein for the first element may also be used.

The first element may have an emission peak wavelength of at least about 401 nm. More suitably, the first element may have an emission peak wavelength of at least about 402 nm, 403 nm, 405 nm, 406 nm or 407 nm. Most suitably, the first element may have an emission peak wavelength of at least about 408 nm, 409 nm, 410 nm, 411 nm or 412 nm. The first element may have an emission peak wavelength of most about 420 nm. More suitably, the first element may have an emission peak wavelength of at most about 419 nm, 418 nm, 417 nm, 416 nm, 415 nm, 414 nm, 413 nm or 412 nm. Most suitably, the first element may have an emission peak wavelength of at least about 407 nm and at most about 417 nm. Each of the above peak emission wavelengths may have a full width at half maximum (FWHM) of 1 nm, 2 nm, 3 nm, 4 nm, 5 nm, 6 nm 7 nm, 8 nm, 9 nm, 10 nm, 11 nm, 12 nm, 13 nm, 14 nm, 15 nm, 16 nm, 17 nm, 18 nm, 19 nm or 20 nm. Each of the above peak emission wavelengths may have a FWHM of at least about 5 nm and at most about 10 nm. For example the peak emission wavelength may be about 412 nm with an FWHM of about 10 nm.

The output of the first element, for example the LED, may have a peak wavelength above 410 nm, but below 420 nm and have a bandwidth such that the lower FWHM wavelength point is above any of: 405 nm, 406 nm, 407 nm. In doing this, the LED can be used to: a) provide visible light that can form part of the overall illumination spectrum of the device; b) provide light that can help kill bacteria but have a less harmful effect on mammalian cells than light having a peak wavelength centered on 405 nm or light from and LED having a lower FWHM spectral point at or below 405 nm. This effect of the 405 nm light is referenced elsewhere herein. Having a peak wavelength range of any of 412-417 nm (or any of the values in at the end of that range or between the end values or any sub range with that range such as 412 nm-415 nm) may help the manufacturing of the device. Light source manufacturing processes may vary, for example different deposition characteristics may occur wafer to wafer or even within the same wafer, leading to a possible variance in output bandwidth in a batch of devices. A further advantage of such a range, over and above the advantages listed as a) and b) above, is that the devices are cheaper to produce due to the increased number of acceptable devices within the same batch. Such advantages may be important when wanting to mass produce a lighting device that poses limited harm to human/mammalian cells but still kills bacteria.

The first element may be any suitable light source emitting in the given active wavelength's, for example, any one or more of, but not limited to: one or more LEDs, one or more broadband light sources with a transmission filter to output the active wavelength's including incandescent lamps and fixtures, fluorescent lamps and fixtures, and high intensity discharge (HID) lamps and fixtures.

The first element may output over 90% of its optical power in a wavelength region above 400 nm. The first element may output over 95% of its optical power in a wavelength region above 400 nm. The first element may output over 98% of its optical power in a wavelength region above 400 nm. The first element may output all of its optical power (100%) in a wavelength region above 400 nm.

The lighting apparatus may output over 90% of its optical power in a wavelength region above 400 nm. The lighting apparatus may output over 95% of its optical power in a wavelength region above 400 nm. The lighting apparatus may output over 98% of its optical power in a wavelength region above 400 nm. The lighting apparatus may output all of its optical power (100%) in a wavelength region above 400 nm.

The lighting apparatus and/or first element may emit substantially no light in the UV.

Outputting most of the light from either the lighting apparatus and/or the one or more first elements above 400 nm helps to ensure that the lighting apparatus emits minimal actinic radiation. This is beneficial for reasons given elsewhere herein.

As described above the active wavelength may be used for limiting the growth of bacteria. This and other benefits of the active wavelengths control is now further described below. The active wavelengths have an efficacy in killing bacteria, fungi and virus'. Examples include using 415 nm light in journal article *The Journal of Infectious Diseases*, 2016, 213(9), 1380-1387; and in particular 405 nm light has been shown to be effective, for example in McKenzie, K. et al. *Microbiology*, 162(9), 1680-1688.

The light emission of the first element of the lighting apparatus can be used to cause cell death in a variety of different bacteria, fungi and viruses. A range of gram-positive as well as gram-negative bacteria and fungi of various genera are susceptible to disinfection with electromagnetic radiation emitted from the first element, including, but not limited to: *Escherichia, Staphylococcus, Coagulase-negative Staphylococcus, Pseudomonas, Bacillus, Clostridium, Streptococcus, Listeria, Acinetobacter, Klebsiella, Proteus, Salmonella, Propionibacterium, Heliobacter, Porphyromonas, Prevotella, Aggregatibacter, Saccharomyces, Candida,* and *Aspergillus.*

Specific species include *Escherichia coli, Staphylococcus aureous,* methicillin-resistant s *Staphylococcus aureous* (MRSA), *Straphylococcus emidermis, Pseudomonas aeruginosa, Bacillus cereus, Bacillus subtilis, Bacillus megaterium, Clostridium difficile, Streptococcus Enterococcus, Acinetobacter baumannii, Pseudomonas aeruginosa, Klebsiella pneumoniae, Proteus vulgaris, Salmonella, Propionibacterium acnes, Heliobacter pylori, Porphyromonas gingivalis, Prevotella intermedia, Aggregatibacter actinomycetemcomitans, Saccharomyces cerevisiae, Candida albicans* and *Aspergillus niger.* Specific strains include, but are not limited to: *Staphylococcus aureous* NCTC 4135, MRSA-US-300 of CA-MRSA, IS853 of HA-MRSA, *Straphylococcus emidermis* NCTC 11964, *Bacillus cereus* NCTC 11143, *Clostridium difficile* NCTC 11204, *Acinetobacter baumannii* NCTC 12156, *Pseudomonas aeruginosa* NCTC 11143, *Klebsiella pneumoniae* NCTC 9633 and *Proteus vulgaris* NCTC CN 329.

The lighting device may also be used to sanitise a range of viruses including Norovirus (NoV) and *Feline calicivirus.*

The mechanism of action resulting in bacterial, fungal and viral disinfection is believed to involve the photo-generated production of reactive oxygen species that causes cellular damage. More specifically, nucleic acids which are the fundamental building blocks of DNA may be attacked by the reactive oxygen species and decomposed so that the cellular or viral machinery is inactivated ultimately causing cell death. The reactive oxygen may also be able to react with the cell membrane, polysaccharide capsule, affecting the cellular integrity and therefore inactivating the bacteria, fungi.

The first element may comprise a semiconductor component comprising a p-n junction and outputting light using electroluminescence. The output light may be substantially incoherent and is preferably operated in a continuous wave regime, but can, if required be pulsed.

The first element may be a Light Emitting Diode (LED). The LED may be formed of any suitable material and be manufactured and assembled in any suitable process. The LED may comprise a compound semiconductor material such as, but not limited to, Gallium Nitride (GaN). Other material systems for the LED may be any of: Indium Gallium Nitride (InGaN), Gallium Arsenide (GaAs), and Indium Phosphide (InP). The compound semiconductor material used to construct the LED may be grown on a suitable substrate such as, but not limited to, Silicon, Silicon Carbide, Gallium Nitride and sapphire. Organic LEDs (OLEDS) may be used. The OLED may comprise $Alq_3$ and derivatives, triphenylamine and derivatives, perylene and derivatives, rubrene and derivatives and quinacridone and derivatives. The OLED may comprise electrically conductive polymers such as derivatives of poly(p-phenylene vinylene) and polyfluorene. The electrically conductive polymer may comprise poly(N-vinylcarbazole) as a host material to which an organometallic complex is added as a dopant, for example Iridium complexes such as $Ir(mppy)_3$. The OLED may comprise a hybrid transparent organic film, polycarbonate, PMMA, PVC, containing a mix of organic dyes such as a push-pull based coumarin and DCM ([2-[2-[2-(dimethylamino(phenyl]ethenyl]-6-methyl-4H-pyran-4-ylidene]-propanedintirile). The OLED may be driven electrically or by another light source such as a laser.

The diode may be a step recovery diode, also known as snap off diode, charge storage diode or varacator diode. Such a diode is a semiconductor junction diode having the ability to generate extremely short pulses. This enables the device to be run at a pulsed rate (not perceivable by the human eye) to enable energy efficiency whilst efficacy with respect to bacterial kill by active part of the emitted spectrum is maintained.

The fabrication may be accomplished using standard deposition techniques such as, but not limited to: Metalorganic Vapour Phase Epitaxy (MOVPE) also known as Metalorganic Chemical Vapour Deposition (MOCVD). The grown structures are then processes in standard semiconductors photolithographic, metallisation and etch processes.

A plurality of LED's may be formed on a common substrate and then separated as part of the manufacturing process. A plurality of LEDs dies may be separated from the rest of the LEDs on the same wafer such that the separated LEDS are co-located on a common portion of the substrate. The separated portion of the substrate may be used to form the first element, i.e. the first element may comprise a plurality of LED dies formed in the same fabrication process.

The active region of the LED chip may comprise one or more quantum wells. These quantum wells may be sandwiched between cladding layers. For example, the quantum wells may be InGaN and the cladding layers may be GaN. The relative In/Ga fraction in the InGaN quantum wells as well as the number and structure of the quantum wells may be selected to provide the desired wavelength range of operation.

The LED die may be housed in a case, thus forming the LED component. The case may comprise an epoxy material and may be shaped to form a lens. The case may comprise one or more light diffusing structures formed upon it. The second (light emitting) element may be coated upon the inside, and/or outside, and be held within the case. Additionally, or alternatively the second element may be located remote to the case, for example the phosphor may be a remote phosphor.

LED die may be packaged in any number of suitable ways including but not limited to in a plastic leaded chip carrier (PLCC) or directly bonded onto a ceramic substrate. The packaged LEDs may be placed on a suitable printed circuit board (PCB) material with suitable heat transfer features such as a heat sink or other features with heat dissipation properties.

The operating voltage of the LED may be between 1V-5V. For example, the turn on voltage may be between 2.5V-4.5V for an LED running at 20 mA.

The first element may be tunable by adjusting the drive current. The drive current (forward current) may be at least about 1100 mA and at most about 1500 mA. Typically, the drive current may be at least about 1450 mA, 1400 mA or 1350 mA. The drive current may be at most about 1450 mA, 1400 mA or 1350 mA. For example the drive current may be between 1200 to 1350 mA. Suitably the drive current may be about 1350 mA. More suitably the drive current may be about 1200 mA. The lumen of the first element may be tunable by adjusting the drive current.

The first element may be a laser diode. The laser diode may comprise gallium nitrite (GaN) or indium gallium nitrite. Organic semiconductor lasers may be used. Such organic semiconductor lasers may use laser dye solutions as their gain material for example laser dye-doped polymers, laser dye-doped oromosil, or laser dye doped-nanoparticle matrices. The use of laser diodes may be advantageous as they may give rise to brighter, clearer and more energy efficient lighting systems.

In an alternative example the first element which may be an organic or inorganic LED may be pumped by a laser rather than by electrical current.

The Second Element

The light output by the first element may be further output from a second element. There may be a plurality of second elements. For example the second element may be a refracting element or a reflecting element such as that described for FIG. 7 below. The example of FIG. 7 may therefore be modified so that the phosphor coating is not present and the second element is the reflector.

The second element may be a filter such as a UV filter described for FIG. 1b below. A lighting apparatus similar to that of FIG. 1b may therefore be made with no phosphor coating wherein the second element is only the filter.

A lighting apparatus may have a colour converting material as one second element and one or further second elements such as a reflector or filter.

As described above, the second element may be one or more phosphors that use at least a portion of the output light from the first element in the process of photoluminescence. The second element may also be any other material or structure that converts the colour of the first element to the desired light output spectrum. The second element may in principle comprise any other light emitting device having an emission spectrum different to that of the first element. This may in principle be a broadband light source such as an incandescent lamp that is not an LED or a light source using another form of luminescence. This source, for example an incandescent lamp, is preferably filtered so that it does not output UV light.

The light output of the second element may be visible light.

An advantage of using a portion of the light emitted from the first element in a photoluminescence process to emit the other wavelength of the spectrum, is that the lighting control for the whole lighting apparatus emission spectrum, including the active wavelengths, may be controlled through controlling the first element only. This simplifies the lighting design and reduces any costs of and technical complexities of having to control multiple light sources.

The second element may comprise phosphors emitting a range of wavelengths, for example wavelengths longer than 420 nm. Examples of different phosphors are now described below.

A yellow phosphor material may be used for the second element which may be cerium-doped yttrium aluminium garnet (Ce3+:YAG).

The phosphor or quantum dot may have a patterned surface. This patterned surface may be obtained by laser etching. A patterned phosphor or quantum dot surface may be advantageous as it allows for enhanced color temperature uniformity at various drive currents. The second phosphor element may therefore be one or more layers comprising a plurality of phosphor elements that are spaced apart from each other such that light from the first element (e.g. an LED) may: a) be incident upon the said phosphor elements; and, b) be output from the device by passing through the spaces between the said phosphor elements.

The phosphor material may be in the nanometer size range. Nanophosphor materials may be YAG:Ce nanophosphor, Y2O3:Eu nanophosphor, LaPO4:Ce,Tb, nanophosphor, Y(V,P)O4:Eu nanophosphor, Y(V,P)O4:Tm nanophosphor, or YVO4:Eu nanophosphor as described in Roman Kubrin, Nanophosphor Coatings: Technology and Applications, Opportunities and Challenges, KONA Powder and Particle Journal, 2014, Volume 31, Pages 22-52.

The nanometer sized phosphor material may be arranged in an array of dots being located above the diode material (i.e. the light source) such that a portion of the light emitted by the diode directly contributes to the overall emission spectrum of the lighting apparatus. Using such a set-up the layer thickness is reduced which is advantageous for heat dissipation.

By using nanostructures benefits can be achieved in emission wavelength by extracting specific emission colors in defined directions, thereby controlling the angular and spectral distributions of emitted light without diminishing significantly the device efficiency as it would be the case using optical filters. Therefore optical filtering may not be required when using nanostructured phosphors.

An additional advantage of using nanostructured phosphors (or nano-antenna-enhanced emission materials, if used) is that it reduces the phosphor-layer thickness or general phosphor material volume compared to a single thick layer of phosphor, which is important with regards to heat dissipation and allowing the diodes emittance to be used as part of the colour mix as opposed to it being absorbed by the phosphor layer completely. Also light emitted by nanoscale phosphor is more easily focusable. The chip level may be made from strong high index contrast dielectric grafting material made by optical immersion lithography. A metallic film (e.g. gold, silver, platinum) may be grown over a subbase, silicon or on any transparent light absorbing material.

Metallic arrays and phosphors, such as dye molecules or quantum dots may enable the use of layers that are much thinner than standard YAG:Ce pallets, resulting in improved heat management and high extraction efficiencies allowing a short wavelength to pump a phosphor and achieve reasonable light output. Metallic nanostructure may support plasmonic resonance via strong light matter interaction which may facilitates control over light emissions without requiring external secondary optical components such as filters and phosphors (nano etched). Quantum dot materials may be $Zn_2SiO_4$:Mn, green-BaMgAl 10 O 17: Eu+ (BAM), blue and $Y_2O_3$:Eu$^{3+}$, red amongst others.

The second element may output light of a wavelength of at least about 420 nm, typically about 570 nm, suitably about 605 nm. The second element may output light at a wavelength of at most about 700 nm typically about 625 nm, typically about 650 nm, suitably about 700 nm.

Red, green and blue phosphors may be used to produce a complete spectrum that is close to daylight with 4000K and 5000K distributions which are very close to natural light. A yellow (green and red) phosphor may be used which mixes with the light emitted from the first element to generate light in the blue, green and red spectrums if that is required for particular applications where white light is not the most suitable illuminating spectrum. For example, in some night working areas it may be more appropriate to work under a red light which does not affect the eyes night light receptors.

Phosphors may be used that comprise orthosilicate, silicate and aluminate materials. Phosphors may be KSF phosphor, GAL (Aluminate) phosphor, silicate phosphor, NYAG (Garnet) phosphor, nitride phosphor and oxynitrite phosphor.

The phosphors may include heavily modified YAG phosphors which may be coated over a 456 nm or a first element die (for example a 405 nm LED die). If the lighting apparatus includes further light emitting elements such as one or more LED dies emitting different peak wavelengths than the first element, then the phosphors may use the light emitted from these other light sources. For example, if another LED die emitting between 430-470 nm were implemented into the same lighting apparatus, the phosphors may utilise light emitted from this further die.

The phosphor material may be coated and/or embedded in another material such as silicone. The phosphors may be deposited in one layer or multiple layers stacked on-top of each other in typical thicknesses of about 20-40 microns (μm). Different phosphors and/or different phosphor densities may be used in different layers. Using several phosphor layers of distinct colours broadens the emitted spectrum, effectively raising the colour rendering index (CRI).

The phosphor layer may be deposited in a thickness of at least about 15 μm, typically about 25 μm and suitably about 20 μm.

The phosphor layer may be deposited in a thickness of at most about 40 μm, typically about 35 μm, suitably about 30 μm.

The second element may be a remote phosphor wherein the phosphors are integrated in a material that is spatially separated from the first element. These remote phosphors are typically integrated into polycarbonate and PMMA (polymethyl methacrylate) and formed into thin shaped layers that cover one or more LEDs.

In devices where the phosphors are directly coated onto the LED, elastomers for example silicone, are typically used as the material to contain the phosphors.

There are advantages to the use of remote phosphors as they can prolong the lifespan of the lighting apparatus by removing heat from the electronic element, the LED. Having the phosphors remote from the LED die may slow down the rate at which the phosphor layer degenerates. Remote phosphors provide more diffuse light, which is desirable for many applications. Remote phosphor designs are also more tolerant of variations in the LED emissions spectrum.

Increased system efficiencies are also benefits that result from reducing the operating temperature of the lighting system. Better colour stability may be attained with longer life of the phosphors. There is typically less glaring than phosphor coated LED's and more consistent flux output and correlated colour temperature for the products. This is because since various wavelength 'bins' can be used to produce light with consistent characteristics.

The output spectrum of the lighting apparatus comprises at least a portion of the light emitted by the first element and at least a portion of the light emitted by the second element. The first element may have one or more output optical paths that extend from the first element to the outside of the lighting apparatus. The second element may be positioned in the output optical path of the first element. The second element and any housing or material accommodating the second element may be at least partially transparent in the active wavelength range such that at least a portion of the active wavelength emitted by the first element is output from the lighting apparatus.

The light apparatus may be configured to not emit actinic radiation. The apparatus may therefore emit only visible light, for example light from 400 nm-700 nm or 401 nm to 700 nm. As such the light emitted from a combination of the first and second elements has substantially no radiant flux (power from all EM waves) that is not attributed to luminous flux. Therefore, substantially all of the radiant flux of the lighting apparatus is within the above said wavelength ranges. In some examples less than 5% of the optical power output from the lighting apparatus is below 400 nm. In some examples less than 2% of the optical power output from the lighting apparatus is below 400 nm. In some examples less than 1% of the optical power output from the lighting apparatus is below 400 nm.

The second element may emit substantially no actinic radiation. The second element may output over 90% of its optical power in a wavelength region above 400 nm. The second element may output over 95% of its optical power in a wavelength region above 400 nm. The second element may output over 98% of its optical power in a wavelength region above 400 nm.

The color rendering index of a lighting apparatus comprising first and second elements may be at least 60 or 70, suitably 80 and most suitably 95.

The color temperature of a lighting apparatus comprising first and second elements may be 2600K, 2900K, 3700K, 4700K, between 2600-4700K, between 2600-7000K and typically 7000K.

FURTHER EXAMPLES

The following are examples of the lighting apparatus. Each of the respective examples may be modified according to any of the optional features and configuration presented herein.

In any of the examples, LEDs dies may be packaged in a plastic leaded chip carrier (PLCC) or on a ceramic substrate. The packaged LEDs may be placed on a suitable printed circuit board (PCB) material with suitable heat transfer features such as a heat sink or other features with heat dissipation properties. The following examples assume the first elements is an LED having a peak emission wavelength of 405 nm, however other first elements and other peak emission wavelengths described herein may be used. The following examples also assume a yellow YAG based phosphor being used as at least one of the second elements; however other second elements described herein may be used.

At 405 nm the LEDs may not be optimally efficient and so should be seeing around 40-45% wall plug efficiency (electric power in v. Light power out). This means that a 3500 W system sufficient to generate appropriate lux levels for anti-bacterial effectiveness, will generate between 2,100-2,000 W of heat which will need to be dissipated in the system.

The first element may be equipped with at least one heat sink which transfers the heat generated by the device away to a fluid medium, for example air or a liquid cooling agent, due to its large surface area. The heat sink may be made of aluminium, copper and/or aluminium alloys. Because the first element is of a shorter wavelength than a blue light source operating at longer wavelengths (for example 450-470 nm), the first element may produce more heat than a commonly used blue element for the same optical output power. For example, an LED outputting light at 405 nm may produce more heat for a given output optical power than a 470 nm LED. Ideally, this heat should be dissipated.

Preferably, the first element is physically linked with at least one extrusion heat sink to that there is a thermally conductive connection between the first element and the heat sink. The heat sink may comprise, for example, an aluminium extrusion. This is advantageous because of its capability of dissipating large heat loads. Alternatively, the first element may be directly attached to a heat sink in combination with a fan (HSF systems). The fan moves air across the heat sink and may also move hot air away from the device. The fan may be integrated inside or on the heat sink or simply directly attached to the heat sink so that the heatsink is in thermal contact with the first element and the fan is in direct contact with the heatsink. The fan may also be remote from the heat sink.

Preferably, a thermally conductive tape or epoxy is used to bring the first element in thermal contact with the heat sink. These two solutions are cost effective and very easy to handle. Alternatively, clips, wire form Z-clips, push pins with compression springs and/or fixing screws may be used to directly attach the first element to the heat sink as well as the fan to the heat sink. These attachment solutions may use holes in the board or solder anchors.

FIG. 1 is a schematic example of a lighting apparatus 2 comprising an LED first element 4 and a second element 6 in a housing 8. For devices where a phosphor second element 6 is used, the phosphor layer may be coated directly onto the LED 4 or alternatively the phosphor 6 may be located remotely above the LED 4. Filters and reflectors may also be used as the second element 6, either as a further second element or instead of the phosphor.

FIG. 1a shows an example of an LED light source 102 comprising a phosphor layer 106 coated upon an LED die 104. The LED die 104 comprises one or more output facets (not shown) from which light is emitted. Any one or more, preferably all, the light output facets are coated with one or more layers of material. These layers comprise phosphors 106 that absorb at least a portion of the output light from the LED chip and in turn, through photoluminescence, emit light at longer wavelengths than that emitted by the LED chip 104. The emission of light from the phosphor layer 106 emits light outwardly and away from the LED chip and, upon viewing or detection in the local environment, may mix with the light emitted from the LED chip 104. In the example of FIG. 1a, the LED chip 104 emits light having a peak wavelength of light of 405 nm-410 nm, preferably 405 nm although in principle other peak wavelength of operation are possible including between 400-420 nm, 400-419 nm, 401-420 nm, 401-419 nm. The phosphors 106 in this example are yellow phosphors as described elsewhere herein. The combined light that is output from the coated LED chip therefore represents a white light.

FIG. 1b shows an example of a lighting device 202 comprising the LED light source of FIG. 1a located on a board 110 and having a housing 108. Any of the details presented for this example for the LED and phosphor coating may be used for the example in FIG. 1a. Furthermore, any of the details described for FIGS. 1a and 1b may be applied to the example of FIG. 7.

The board 110, in this example of FIG. 1b, is a PCB comprising electrical features that allow electrical power and/or electrical control signals to pass from the PCB to the LED chip 104. The LED chip 104 and the PCB are therefore in electrical connection. The electrical current supplied to the LED chip 104 is used by the LED to power the light emission of the LED chip 104. In this example the LED chip 104 is supplied with continuous electrical current in the ON state so that the white light emission from the coated LED 102 continually contains light emitted from the LED chip whilst electrical power is provided to the lighting apparatus 202. The PCB may have other electrical elements such as controllers and electronic processors for sending control signals to the LED chip 104. The PCB in this example is opaque to the wavelengths of light output from the LED chip and phosphors. The PCB also has (not shown) a heat sink to remove unwanted heat from the LED chip 104 and heat generated by the phosphor layer 106 that conducts through the LED chip 104. Similarly to FIG. 7, the example of FIG. 1b may be further provided with one or more reflecting elements (not shown) that receive at least a portion of the light output from at least the LED (and optionally the phosphor) and reflect the received light towards an exit aperture of the lighting device. The exit aperture may have one or more sets of optics used to focus, disburse and/or filter the light. An example of this are lenses that form part of the outer housing of the device.

The housing 108 in this example of FIG. 1b comprises a substantially transparent (to the desired wavelengths of operation) body that extends around, but does not contact, the LED 104 chip and phosphor layer 106. FIG. 1b shows a cross section of this overall lighting apparatus 202 wherein the housing 108 is attached to the PCB 110, thus surrounding at least a portion of the LED chip 104.

The gap 112 between the coated LED and the housing may be air filled or filled with another gas. The gap 112 may also be filled with a visibly transparent encapsulation compound as described elsewhere herein.

The LED chip 104 is mounted upon the PCB 110 so that the phosphor layer 106 is located remote from the PCB 110. In this example the phosphor layer 106 is coated on a surface of the LED 104 that is parallel but spaced apart from the PCB insofar that the phosphor 106 does not contact the PCB. In other examples, the phosphor layer 106 may be coated on one or more other surfaces of the LED chip 104. Other variations of FIG. 1b could have the phosphor containing material deposited onto the LED such that all of the faces of the LED not adjacent to the PCB board are covered in the phosphor material.

The housing 108 may be coated with a thin film filter 114. The filter 114 may have a stack of one or more material layers designed to optically filter out actinic radiation. The UV filter 114 may equally be located on the inside of the housing, within the housing 108, located on a further coating directly applied to the LED chip 104 or on another structure of the light emitting device. The filter may be, but is not limited to, a bandpass filter or an edge filter. The UV light filtered by the filter may be in any of the UV ranges described herein. The spectral edge of the filter may be configured to filter out any of: over 90% of the UV light emitted by the LED 104; over 95% of UV light; over 98% of the light emitted by the LED 104. Having the lighting apparatus 202 emit light with substantially no actinic radiation may enable the device to be used more readily in environments where humans are present.

The LED die may emit a peak wavelength between 408-412 nm and have a bandwidth of between 10-18 nm (or FWHM of 2.6-4.7 nm). In these examples, the light emitted by the LED chip 104 may emit sufficiently low levels of actinic radiation that the UV filter 114 is not required. The UV filter 114 described for this example may be used in other examples described herein.

The LED die may emit a peak wavelength between 407-417 nm and have a bandwidth of +/−5 nm (or a FWHM of 10 nm). The peak wavelength may be 412 nm with an FWHM of 10 nm. In these examples, the light emitted by the LED chip 104 may not emit any actinic radiation so that the UV filter 114 is not required. Other possible wavelength ranges are disclosed herein.

The lighting apparatus 202 of FIG. 1b comprises electrical connections and mechanical features (not shown) for electrically coupling and physically coupling to a light fitting, for example on a ceiling light fitting. The lighting device may comprise other mechanical, optical or electrical components. For example the lighting apparatus 202 may be a lamp that may have its own electrical wired cable for plugging into an electrical power outlet.

A method of assembling a lighting apparatus, such as that shown in FIG. 1a includes depositing the second element on the first element. The first element is typically an LED and the second element is typically a material having one or more phosphors.

A method of assembling a lighting apparatus, such as that shown in FIG. 1b, includes locating the first and second element in a housing. This method may use the steps of forming the lighting apparatus of FIG. 1a.

Any of these methods may further include steps to identify the first element by a sorting process described elsewhere herein. The method may further comprise sealing the housing after locating the first and second elements in the housing. Sealing the housing may be done in any way including but not limited to thermal bonding, adhesive bonding, soldering or mechanical based seals sealing. The seal may be achieved be sealing the PCB to the housing.

FIG. 2a illustrates an example lighting apparatus 302, wherein the first element is an LED 304 and the second element is a remote phosphor layer 306 which surrounds the LED 304 from three faces to allow more efficient conversion of the color of the first element 304 to the desired light output spectrum. The LED lighting apparatus 302 may also be placed into a housing (not shown) such that the LED 304 and the remote phosphor 306 are both located within the housing.

FIG. 2*b* illustrates an example of the lighting apparatus 402 of FIG. 2*a* having an LED first element 404 and a phosphor layer second element 406 located on a substrate 418 for attaching to any suitable light fitting. Substrate 418 is typically a printed circuit board. The PCB typically comprises a copper clad laminate material including FR4, FR1, CEM1 or CEM3. Spacing upstands 416 extend outwardly and away from the PCB board and attach to the phosphor layer second element 406. This allows for the phosphor 406 to be located remotely above the LED 404. In other variants of FIG. 2*b*, the phosphor layer 406 may be located directly on top the LED 404 (not shown). The LED lighting apparatus 402 may also be placed into a housing (not shown).

FIG. 2*c* illustrates another example of the lighting apparatus 502 2*a* comprising an LED first element 504 and a phosphor layer second element 506 having an encapsulant 512 between the first 504 and second elements 506. The encapsulant 512 is an active wavelength-transparent moulding compound and may comprise polymers such as but not limited to polyurethane, silicone and epoxy resins and combinations thereof. The LED 504 is located on a suitable PCB material substrate 518 that has features for attaching to a light fitting. The attachment features may integrally formed as part of the PCB or may be attached to it. The phosphor layer 506 is located remotely above the LED 504 or surrounding the LED 504 from three faces. The LED lighting apparatus 502 may also be placed into a housing (not shown). The phosphor layer 506 may be deposited to the inside of the housing which can be of rectangular or semi-circular shape.

FIG. 2*d* illustrates another example of the lighting apparatus 602 similar to FIG. 2*c* wherein the second element 606 is a phosphor layer which is directly coated on the first element which is a LED 604. The LED lighting apparatus is placed into a housing 608. Optionally the lighting apparatus may also contain at least one lens and/or filtering elements, such as a UV filter (not shown). Lens materials can be polymers such as but not limited to polymethylmethacrylate (PMMA), polycarbonate (PC), cycloolefin copolymer (for example Zeonix), polymethacrylmethylimid (pmmi, Pleximid), optical silicone resins and glass. These lens materials may be used with other examples of the lighting apparatus described herein.

FIG. 2*e* illustrates the example of the first element 704 and second element 706 of FIG. 2*d* without an outer housing and having an attachment means 720 for retro fitting purposes. The attachment means 720 material can but is not limited to electrically conducting materials such as metals and semiconductors and more specifically but not limited to any of: aluminium, aluminium alloys, steel (for example cold rolled steel and stainless steel), copper, copper alloys (for example brass).

FIG. 3 illustrates an example of the lighting apparatus 802 comprising a remote phosphor layer 806 and three LEDs 804*a*, 804*b*, 804*c*. The LEDs 804 are located on a PCB substrate 818 for attaching to any suitable light fitting. Spacing pillars 816 allows for the planar phosphor layer 806 to be located remotely above the LEDs 804. Any sufficient number of LEDs 804 may be used to achieve the desired effect of bacterial, fungal and viral kill.

FIG. 4 illustrates an example of an LED 902 and phosphor layer for use with the lighting apparatus. The LED semiconductor layer 904 is disposed on top of a substrate or wafer 922. LED substrate or wafer materials may be but are not limited to sapphire, silicon carbide (SiC), Gallium nitride (GaN) or silicon. A phosphor layer 906 is coated directly on top of the semiconductor material 904, particularly covering the output facets from which light is emitted from the LED 902. The phosphor layer 906 can also be incorporated into a flexible in mold decoration film which may be made of a flexible elastomer material like silicone. However, the phosphor layer 906 may also be located remotely (not shown). The semiconductor layer 904 comprises contact points 924*a*, 924*b* for electrically connection to an external electrical power supply. The contact points 924 may be electrically connected via wire bonding. Contact point 924 materials may be but not limited to aluminium, aluminium alloys, steel (for example cold rolled steel and stainless steel), copper, copper alloys (for example brass).

FIG. 5 shows an example of an output spectra of the lighting apparatus with two distinct peak emission wavelengths, wherein the first element emits at a peak wavelength of 405 nm and the second element emits at a peak wavelength which is longer than that of the first element. The first element in this example is a LED and the second element is a phosphor layer.

FIG. 6 illustrates the use of the lighting apparatus 1002 (not to scale) in residential and commercial spaces having multiple objects and surfaces 1026. The lighting apparatus 1002 comprising an LED first element 1004 and a phosphor second element 1006 which is directly coated onto the LED 1004 in a housing (1008). The lighting apparatus having an attachment means 1020 for retro fitting purposes.

FIG. 7 illustrates a lighting apparatus 1102 comprising a phosphor coated LED 1104 similar to that of the example shown in FIG. 1*a* or 1*b*. The lighting apparatus 1102 in this example also comprises primary and secondary optics.

This example of a lighting apparatus comprises an LED first element 1104 and phosphor second element 1106 which is directly coated onto the LED first element 1104, both of substantially cylindrical shape, however the LED can be of other shapes such as a rectangular chip shape. The phosphor coating may also in one variation be coated over all surfaces of the LED apart from the LED surface contacting the PCB. The LED 1104 first element is mounted onto the PCB board 1110 along a central axis which is normal to the PCB board. The PCB board 1110 provides electrical connectivity to the LED. The LED 1104 and the phosphor 1106 extend upwardly along the central axis from the PCB board 1110.

The LED 1104 and the phosphor second element 1106 are surrounded circumferentially along said central axis by a truncated conical hollow housing 1108, wherein the housing is truncated at the narrow end to form a ring-shaped base surface which is mounted onto the PCB board 1110. The wider end of the truncated hollow conical housing 1108 has a ring-shaped surface that defines the head portion of the lighting apparatus which is covered by a disc-shaped transparent lid 1138 through which light from the phosphor coated LED exits the lighting apparatus.

Multiple lenses 1132*a*, 1132*b* and refracting surfaces 1130*a*, 1130*b*, and 1130*c* are used to collimate the light with the aid of surface 1134 which reflects light from the phosphor coated LED towards the lid 1138.

The LED 1104 and the phosphor 1106 are cylindrically surrounded along the central axis by a tubular element providing for refracting surface 1130*c*. The primary lens 1132*a* is a convex lens and mounted onto or internally formed within the tubular element to focus light onto the secondary convex lens 1132*b*.

The transparent lid 1138 has a cylindrical aperture along the central axis to accommodate the secondary optics comprising the secondary lens 1132b and refracting surfaces 1130a and 1130b. The refracting surfaces 1130a and 1130b may be part of a truncated hollow conical refracting element which surrounds the secondary lens 1132b circumferentially along the central axis. The hollow conical refracting element comprising the refracting surfaces 1130a and 1130b is truncated at the narrow end having a ring-shaped base surface which is mounted to or internally contained within the transparent lid 1138. The secondary lens 1132b is mounted to or internally contained within the wide end of the truncated hollow cone and may be a convex lens.

Lens materials can be polymers such as but not limited to polymethylmethacrylate (PMMA), polycarbonate (PC), cycloolefin copolymer (for example Zeonix), polymethacrylmethylimid (pmmi, Pleximid), optical silicone resins and glass. The refracting surfaces 1130a, 1130b and 1130 may be made of polymers or glass for example acrylic, polycarbonate or borosilicate glass.

The side walls 1134 of the truncated conical housing laterally extending from the LED 1104 light source at an angle between the PCB board 1110 and the transparent lid 1138 are reflective and may be manufactured by faceting, segmenting or coating of the inner surface of the housing 1108 with for example aluminium or reflective polymers. Additionally or alternatively, the housing sidewalls may have one or more diffracting surfaces to direct light onto the secondary optics, such as a secondary lens. The sloped sidewall reflector in this example is appropriately angled with respect to the secondary optics, primary optics and the LED to direct light through the secondary optics and out of the lighting device.

In this example the secondary optics 1136 comprises an optical transmission element comprising a central lensing portion 1132b for receiving light from the first primary optics 1132a and transmitting the said light out of the apparatus into the local environment, for example a room. The secondary optics 1136 form part of the housing 1108 of the lighting apparatus 1102 and a portion of the it span between sidewalls 1134. The secondary optics 1136 in this example resides in a portion of an aperture of the lighting apparatus (defined by the large diameter ring of the said cone) through which light emitted from the phosphor coated LED 1104, 1106 is output. The secondary optics 1136 is symmetrically disposed about an optical axis running normal from the PCB through the centre of the lid 1138.

A first lens component 1132a (primary optics) is used and is located in between the phosphor coated LED 1104, 1106 and the secondary optics 1136. The primary optics may comprise total internal reflection (TIR) optics. In this example the primary optics 1132a comprises a lens 1132a mounted directly on top of the first element 1104 and guides a first portion of the light from the phosphor coated LED 1104, 1106 directly to the secondary optics whilst a second portion of the light from the phosphor coated LED 1104, 1106 passes through the primary optics 1132a to a reflector 1134 which reflects light through the lid, thus outputting a controlled light beam.

It is envisaged that other lighting device structures may be used and that the example shown in FIG. 7 may be modified according to any feature described elsewhere herein, including but not limited to a UV filter disposed on a portion of the housing, for example on an outer and/or inner facing surface of the primary and/or secondary optics.

The lighting apparatus may further comprise one or more third elements that emit light in a wavelength range above 400 nm but having a different peak wavelength than the peak wavelength of the first element.

Where the second element is a phosphor, at least a portion of the light output from the third element may also be used by the phosphor in the photoluminescence process.

The third element and the first element may be controllable independently of each other. For example, the third element may a blue LED. If the lighting apparatus were required at some point in time (for example during the daytime) to light a room normally without needing bacterial neutralisation, then the third element may be turned on and the first element may be turned off. This may lengthen the life of the first element and give a higher brightness to a user because the eye may be more sensitive to the wavelength of the third element. This may also save on electricity costs as the electrical-optical conversion efficiency of the third element may be greater than the first element. The phosphors may also by of a type that more efficiently uses the wavelength of the third element. The turning on and off of the third and first element may be accomplished using a single control input signal that only permits one of the first and third elements to be on at once. The lighting apparatus may therefore have two 'ON' settings: 'Normal lighting', 'bacterial control lighting'.

The third element may emit a longer wavelength than the first element, for example the third element may emit a blue light having a peak emission wavelength between any of 405-495 nm, 420-470 nm. The third element may emit a peak wavelength between 460-470 nm and have a bandwidth of +/−5 nm (or a FWHM of 10 nm). The peak wavelength may be 465 nm with an FWHM of 10 nm.

Figure 8B:
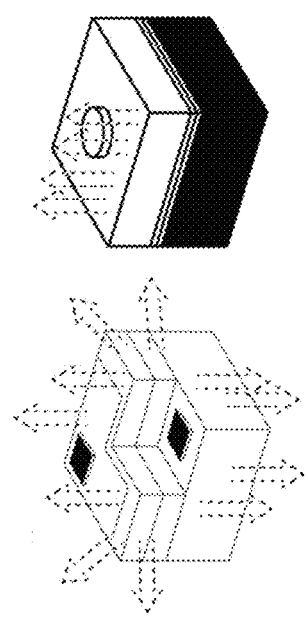
FIG. 8b shows a lighting apparatus having multiple layers.

FIG. 8a illustrates an example lighting apparatus 1202, wherein the first element is an LED 1204 and the second element is a planar remote phosphor layer 1206 which is remotely located above the LED 1204. Between LED 1204 and the remote phosphor layer 1106 sits a transparent substrate 1210. The LED lighting apparatus 1202 is also to be placed into a housing 1208. The remote phosphor maybe deposited onto the transparent substrate 1210. FIG. 8b illustrates an example apparatus comprised of multiple layers. The left hand drawing shows the emittance from sapphire showing emittance loss in multiple directions due to the crystalline properties of the material. Typically about 40% of light emission is lost in such an apparatus due to the inability to efficiently focus the emitted light. The right hand drawing shows gallium nitrite (GaN) on silicon based light source having a directional emittance. Typically about 70% if the emittance from a GaN material is directed toward one direction. Such a light source may be used as the first element in the present application.

FIG. 9a shows a schematic drawing of a lighting apparatus having an emission spectrum dissimilar to sunlight. Such a light emission spectrum can be achieved using a blue first element and blue, yellow and red phosphors. Such a set-up will create white light but the emission spectrum is not very similar to the sunlight's emission spectrum. FIG. 9b shows a schematic drawing of a lighting apparatus having an emission spectrum similar to sunlight. A sunlight emission spectrum can be achieved using a purple or violet light source and blue green and red phosphors. Using a purple light source as first element instead of a blue light source allows for an emission spectrum to be created which is very similar to sunlight emission. The emission spectrum of a lighting apparatus able to provide for such a sunlight emission is comprised of light emitted directly from the light source as well as light remitted by the phosphors. The first element may be an LED. The similarity to the sunlight emission spectrum makes such systems desirable for use in spaces where humans are present such as indoor lighting.

Figure 10B:
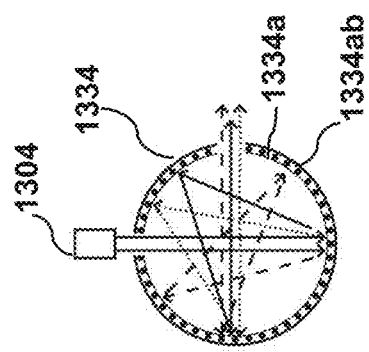
Figure 10A:
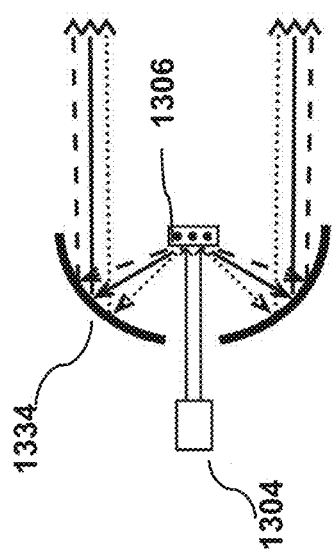
FIG. 10a shows a side view of lighting apparatus having a laser diode first element.

FIG. 10a illustrates a side view of an example apparatus and also shows schematic drawings of light beams, wherein a laser diode 1304 is used as a first element and a remote phosphor plate 1306 is used as a second element. A remote phosphor set-up is desirable due to the high intensity of the laser. The laser diode beam is directed towards the phosphor plate 1306 and the resulting emission from the phosphor plate is collimated with a reflector 1334. Multiple laser diodes for pumping the phosphor may be used.

FIG. 10b illustrates a top view of the example apparatus of FIG. 10a. The reflector 1334 is substantially circular and has a double wall 1334a and 1334b. A small proportion of the substantially circular reflector is discontinuous to allow for the laser beam to enter and for the collimated light to exit. Light entry and exit points are positioned perpendicular to each other.

Figure 11:
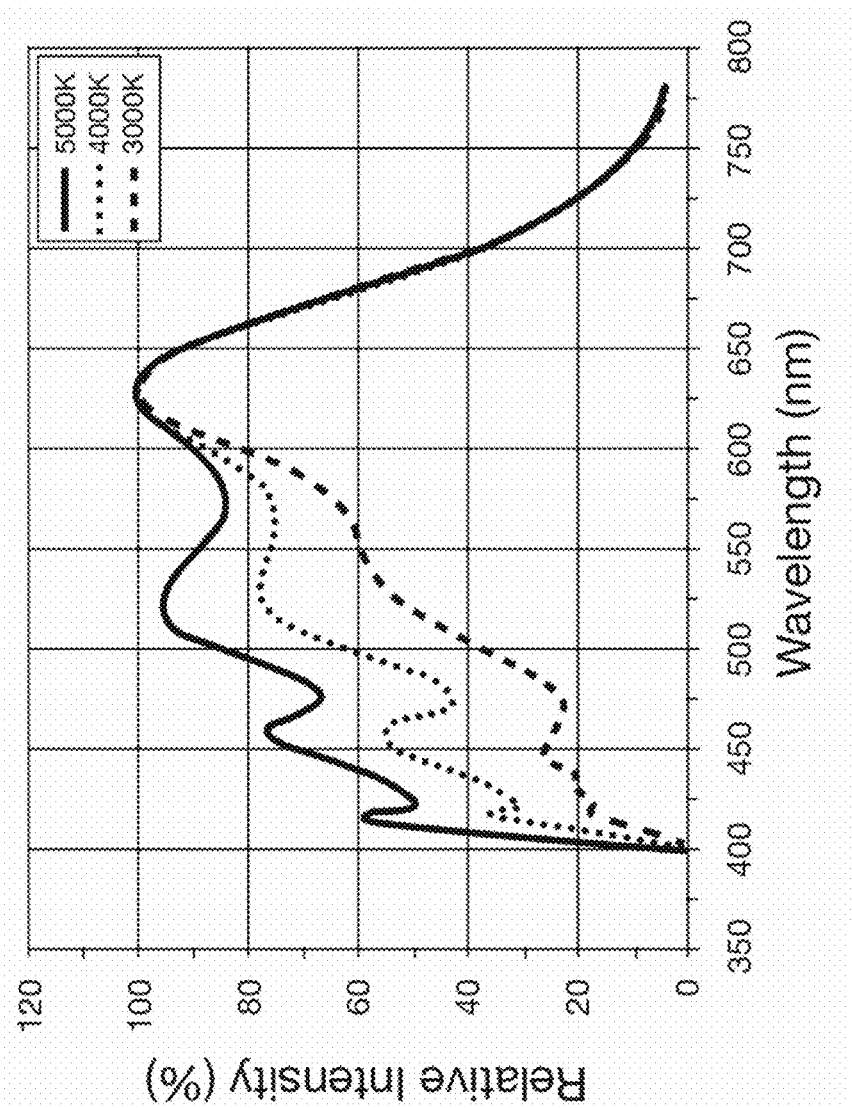
FIG. 11 shows an example of an output spectrum of the lighting apparatus at different color temperatures.

FIG. 11 shows an example of an output spectrum of the lighting apparatus at different color temperatures (5000K, 4000K, 3000K). The spectra show the combined spectra for a 412 nm first element (e.g. LED) pumping the phosphor second element. The different colour temperatures (3000K, 4000K, 5000K) are achieved by adjusting the drive current. The emission of the first element at 412 nm contributes to the overall spectrum of the lighting apparatus (see 412 nm peak at e.g. 5000K and 4000K).

In a specific example the LED may have the technical parameters as outlined in table 1 to table 3 below.

TABLE 1

| $V_f$ bin | Forward Voltage [$V_{DC}$] | Forward current [mA] |
|---|---|---|
| A1 | 23-26 | 1200 |
| A2 | 26-29 | 1200 |

TABLE 2

| Parameter | Minimum value | Typical value | Maximum value | Unit |
|---|---|---|---|---|
| Luminous Flux | 2300-2500 | 2700-2900 | — | lm |
| Correlated color temperature (CCT) | 2600, 2900, 3700, 4700, 2600-4700 | 2700, 3000, 4000, 5000, 2700-5000 | 2900, 3200, 4200, 5300, 2900-5300 | K |
| Color rendering index (CRI) | | 95 | — | — |
| Input voltage ($V_{in}$) | 23 | 26 | 29 | $V_{DC}$ |
| Forward current (IF) | 1200 | — | — | |
| Power consumption (P) | 27.6 | 31.2 | 34.8 | W |
| Viewing angle | 120 | — | — | degrees |

TABLE 3

| Parameter | Value | Unit |
|---|---|---|
| Max. Current ($I_F$) | 1350 | mA |
| Power Dissipation ($P_D$) | 0.48 | W |
| Operating Temperature ($T_{OPR}$) | −40 to +85 | ° C. |
| Storage Temperature ($T_{STG}$) | −40 to +100 | ° C. |

There is presented a method for assembling a lighting apparatus. The lighting apparatus comprises at least a first and second element as described elsewhere herein. The method comprises locating the first and second element in a housing.

The housing may have one or more further optical or electronic components for example: one or more lenses for focusing the light emitted from the first, and optionally second, light emitting element; optical reflectors for reflecting at least a portion of the light output from the first and/or second elements out of the apparatus; optical filters, such as a thin film optical transmission filter for filtering out UV light; electronics for supplying electrical power and/or electronic control signals to drive the first element. Any of these components may be integrally formed as part of the housing or located on or within the housing.

The method may, prior to locating the first and second element in the housing, deposit the second element on the first element. The method may comprise sealing the housing after locating the first and second elements in the housing.

Any one or more of the above steps may be performed manually or by a machine.

The light sources may be separated based on a sorting exercise. For example, a plurality of LEDS may be tested to determine at least one parameter of operation wherein at least one LED that conforms to the selection process is chosen to be one of the first elements in the lighting apparatus.

The parameters may include any one or more of: a peak emission wavelength; a peak emission wavelength for a particular electrical drive condition or range of conditions; electronic power to optical output power efficiency. The parameter may be at least one parameter relating to the wavelength value of a peak wavelength emission.

The selection process may include comparing the measured parameter to one or more rules or criteria, such as, but not limited to one or more thresholds. These thresholds may be upper threshold limits or lower threshold limits or an acceptable range for the specified parameter. For example, the LEDs may be select if their output peak emission wavelength is between any of the ranges of 400 nm-420 nm, or 400 nm to 419 nm, or 401 nm to 419 nm, 407 nm to 417 nm, 411 nm-419 nm, 411 nm-418 nm, or 400 nm-410 nm, or 403 nm to 407 nm, or 405 nm+/−1 nm, or 405 nm+/−0.5 nm.

The testing for any of the parameters may be accomplished when the LEDs are on a common substrate, or when the LEDs are separated into individual components.

A plurality of LEDs may be identified in an area of a substrate used to fabricate the LEDs. The identification may use one or more of the parameters described above, such as but not limited to testing for the wavelength, and optional output power of the peak emission of the output spectra. An area may be identified to yield LEDs with common characteristics because similar fabrication parameters are present in localised areas of the substrate wafer, for example one or more thickness of the semiconductor layers or one or more widths or lengths of a patterned structure wherein widths or lengths may vary due to deposition parameters such as over etching. An area of the wafer substrate containing a plurality of similar LEDS may be separated after testing wherein the separation area is based on the testing. This may therefore provide multiple LED components that can be utilised in different applications. This may particularly be advantageous where the electrical-optical power efficiency of the LED in the wavelength spectrum of interest is low and multiple LED sources are required.

The substrate may form part of the LED die device acting as the first element or may be removed. The substrate may have features that allow the LED to be used and/or fitted into the lighting apparatus. For example, the substrate may comprise any one or more of:

A) one or more electrical tracks for delivering electrical current to the LED. The electrical tracks may include contact points for electrically connection to an external electrical power supply. The contact points may be electrically connected via wire bonding.

B) One or more physical features, such as upstands and/or recesses for engaging with another part of the lighting apparatus. For example, the lighting apparatus may comprise a cap comprising phosphors and the substrate may engage with the cap. This engagement may form part of a permanent fixing or a temporary fixing. Fixing the substrate or even the LED to another part of the lighting apparatus may be accomplished using any fixing feature or technique including, but not limited to, interference fitting, adhesives, thermal bonding, and mechanical interlocking.

The lighting apparatus may be filled at least partially with a material that allows at least for the active wavelength to be transmitted through the material out of the apparatus. For example, first element may be covered by the said material wherein the said material may fill the space between the first element and the second element in a remote phosphor configuration. The material may be a transparent moulding compound such as but not limited to polyurethane, silicone and epoxy resins.

There is also presented light fitting for coupling to a colour conversion material including a phosphor lighting device; the light fitting comprising:
one or more LEDs that have a peak emission wavelength between 400 nm up to but not including 420 nm;
one or more fixing features for coupling the light fitting to the phosphor lighting device such that, when coupled and in use, light emitted by the LED is directly incident upon at least a portion of the phosphors of the phosphor lighting device.

There is also presented a method of fitting the light fitting to a phosphor lighting device; the method comprising coupling the light fitting to the phosphor lighting device.

The method may include a step of removing an existing light fitting coupled to the phosphor lighting device prior to the coupling the new light fitting.

The method may include, prior to or during coupling the new light fitting, at least partially filling the phosphor lighting device with a material at least partially transparent to the active wavelength.

The lighting device may be sealed to the outside environment, for example having features that allow the device to be hermetically sealed. This may be advantageous in a hospital environment where the lighting device is re-used by replacing the first element; for example, if the first element malfunctions. A person may need to replace the first element and/or a fitting that the first element is housed upon, but does not want to open up a lighting device that may have accumulated contaminated air during its life.

The outer surface of the lighting apparatus may be coated with other antibacterial materials or use materials with inherent antibacterial properties. This may make the handling of the device in possible contaminated areas safer, particularly where a person is handling a portion of the apparatus that does not get irradiated by the active wavelength.

What is claimed is:

1. A phosphor lighting apparatus comprising:
(a) a first element that emits light consisting of a peak emission wavelength between 412 nm and 415 nm, wherein the first element consists of a light emitting diode (LED),
wherein the first element emits light with a full width at half maximum (FWHM) of up to 10 nm,
wherein the light emitted by the first element comprises a lower FWHM wavelength that is above 405 nm; and,
(b) a second element comprising phosphors that output and/or convert at least a portion of the light emitted by the first element;
wherein the light output from the phosphor lighting device comprises light emitted from the first element and light emitted from the phosphors;
wherein the phosphor lighting apparatus comprises only one LED; and
wherein the phosphor lighting apparatus is effective in bacterial, fungal, and viral disinfection while having a less harmful effect on mammalian cells than light emitted from an LED having a lower FWHM that is at or below 405 nm.

2. The lighting apparatus of claim 1, wherein the second element emits light comprising longer wavelengths than the peak emission wavelength of the first element.

3. The lighting apparatus of claim 1, wherein the second element comprises phosphors for absorbing light from the first element and emitting light at longer wavelengths than the absorbed light.

4. The lighting apparatus of claim 3, wherein the phosphors comprise a yellow phosphor.

5. The lighting apparatus of claim 3, wherein the second element comprises one or more color converting materials selected from the group consisting of: nitride and/or oxynitride; YAG phosphor, zinc sulfide, zinc selenide, cadmium sulfide, cadmium selenide, cadmium telluride and combinations thereof.

6. The lighting apparatus of claim 1, wherein at least one of the second elements comprises an optical filter for controlling the bandwidth of the emitted light and/or for filtering actinic radiation emitted from the first element.

7. The lighting apparatus of claim 6, wherein the actinic radiation filter is configured to receive light emitted from the first and second elements; and
transmit actinic radiation filtered light for outputting by the lighting apparatus.

8. The lighting apparatus of claim 1, wherein substantially all of the optical output power of the lighting apparatus corresponds to wavelengths above 400 nm.

9. The lighting apparatus of claim 1, wherein the combined output of the first element and the second element is white or a shade of white light.

10. A method for bacterial, fungal, and viral disinfection, comprising:
illuminating a target surface or area with a phosphor lighting apparatus comprising:
(a) a first element that emits light consisting of a peak emission wavelength between 412 nm and 415 nm,
wherein the first element comprises a light emitting diode (LED),
wherein the first element emits light with a full width at half maximum (FWHM) of up to 10 nm,
wherein the light emitted by the first element comprises a lower FWHM wavelength that is above 405 nm; and,
(b) a second element comprising phosphors that output and/or convert at least a portion of the light emitted by the first element;
wherein the light output from the phosphor lighting device comprises light emitted from the first element and light emitted from the phosphors;

wherein the phosphor lighting apparatus comprises only one LED; and wherein the phosphor lighting apparatus is effective in bacterial, fungal, and viral disinfection while having a less harmful effect on mammalian cells than light emitted from an LED having a lower FWHM that is at or below 405 nm.

11. The method of claim 10, wherein the second element emits light comprising longer wavelengths than the peak emission wavelength of the first element.

12. The method of claim 10, wherein the second element comprises a material applied upon the first element.

13. The method of claim 10, wherein the second element comprises phosphors for absorbing light from the first element and emitting light at longer wavelengths than the absorbed light.

14. The method of claim 13, wherein the phosphors comprise a yellow phosphor.

15. The method of claim 13, wherein the second element comprises one or more color converting materials selected from the group consisting of: nitride and/or oxynitride; YAG phosphor, zinc sulfide, zinc selenide, cadmium sulfide, cadmium selenide, cadmium telluride and combinations thereof.

16. The method of claim 10, wherein at least one of the second elements comprises an optical filter for controlling the bandwidth of the emitted light and/or for filtering actinic radiation emitted from the first element.

17. The method of claim 16, wherein the actinic radiation filter is configured to receive light emitted from the first and second elements; and transmit actinic radiation filtered light for outputting by the lighting apparatus.

18. The method of claim 10, wherein substantially all of the optical output power of the lighting apparatus corresponds to wavelengths above 400 nm.

19. The method of claim 10, wherein the combined output of the first element and the second element is white or a shade of white light.

20. A method for limiting the growth of bacteria, fungi and viruses comprising illuminating a target surface or area with a lighting device comprising:
(a) a first LED that emits light consisting of a peak emission wavelength between 412 nm and 415 nm,
wherein the first element emits light with a full width at half maximum (FWHM) of up to 10 nm,
wherein the light emitted by the first element comprises a lower FWHM wavelength that is above 405 nm; and,
(b) a second LED that emits light in a wavelength region above 420 nm,
wherein the lighting device comprises only two LEDs; and
wherein the lighting device is effective in limiting the growth of bacteria, fungi and viruses while having a less harmful effect on mammalian cells than light emitted from an LED having a lower FWHM that is at or below 405 nm.

* * * * *